US006962092B2

(12) United States Patent
Pasquali et al.

(10) Patent No.: US 6,962,092 B2
(45) Date of Patent: Nov. 8, 2005

(54) METHOD AND APPARATUS FOR DETERMINING THE LENGTH OF SINGLE-WALLED CARBON NANOTUBES

(75) Inventors: Matteo Pasquali, Houston, TX (US); Virginia A. Davis, Webster, TX (US); Ingrid Stepanek-Basset, La Grand'Combe (FR); A. Nicholas G. Parra-Vasquez, Oxnard, CA (US); Robert H. Hauge, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 10/836,551

(22) Filed: Apr. 30, 2004

(65) Prior Publication Data

US 2005/0160798 A1 Jul. 28, 2005

Related U.S. Application Data

(60) Provisional application No. 60/467,642, filed on May 2, 2003.

(51) Int. Cl.$^7$ ............................................. G01N 33/00
(52) U.S. Cl. ...................................................... 73/866
(58) Field of Search .............................. 73/866, 432.1; 209/1

(56) References Cited

U.S. PATENT DOCUMENTS

2002/0150524 A1 * 10/2002 Smalley et al. ............. 422/198
2003/0168385 A1 * 9/2003 Papadimitrakopoulos ...... 209/1

OTHER PUBLICATIONS

Iijima, et al., "Single-Shell Carbon Nanotubes of 1 nm Diameter," 363 Nature (1993) pp. 603-605.
Bethune, et al., "Cobalt Catalyzed Growth of Carbon Nanotubes with Single Atomic Layer Walls," 363 Nature (1993), p. 605.
Saito, et al., "Physical Properties of Carbon Nanotubes," London: Imperial College Press (1988).
Sun, et al., "Creating the narrowest carbon nanotubes", 403 Nature (2000), p. 384.
Qin, et al., "Electron microscopic imaging and contrast of smallest carbon nanotubes", 349 Chem. Phys. Lett. (2001), pp. 389-393.
Wang, et al., "Single-walled 4 A carbon nanotube arrays", 408 Nature (2000), pp. 50-51.

(Continued)

Primary Examiner—Hezron Williams
Assistant Examiner—Tamiko Bellamy
(74) Attorney, Agent, or Firm—Ross Spencer Garsson; Edward T. Mickelson; Winstead Sechrest & Minick P.C.

(57) ABSTRACT

The present invention is directed to at least one method and at least one apparatus for determining the length of single-wall carbon nanotubes (SWNTs). The method generally comprises the steps of: dispersing a sample of SWNTs into a suitable dispersing medium to form a solvent-suspension of solvent-suspended SWNTs; determining the mean SWNT diameter of the solvent-suspended SWNTs; introducing the solvent-suspended SWNTs into a viscosity-measuring device; obtaining a specific viscosity for the SWNT solvent-suspension; and determining the length of the SWNTs based upon the specific viscosity by solving, for example, the Kirkwood-Auer equation corrected by Batchelor's formula for the drag on a slender cylinder for "L," to determine the length of the SWNTs. The apparatus generally comprises: a SWNT sample introduction mechanism; a dispersal chamber; a SWNT radius-determination chamber; and a viscosity determining chamber, wherein the SWNT sample introduction mechanism, the dispersal chamber, the SWNT radius-determination chamber, and the viscosity determination chamber are each operatively connected to at least one of the others.

21 Claims, 6 Drawing Sheets

OTHER PUBLICATIONS

Hafner, et al., "Catalytic growth of single-wall carbon nanotubes from metal particles", 296 Chem Phys. Letters (1998), pp. 195-202.

Cheng, et al., "Bulk morphology and diameter distribution of single-walled carbon nanotubes . . . ", 289 Chem. Phys. Letters (1998), pp. 602-610.

Nikolaev, et al., "Gas-phase catalytic growth of single-walled carbon nanotubes from carbon monoxide", 313 Chem. Phys. Letters (1999), pp. 91-97.

Thess, et al., "Crystalline Ropes of Metallic Carbon Nanotubes", 273 Science (1996), pp. 483-487.

Vander Wal, et al., "Flame and furnace synthesis of single-walled . . . ", J. Phys. Chem. B 105(42) (2001), pp. 10249-10256.

Wong, et al., "Carbon nanotube tips: high resolution probes for imaging biological systems", 120 J. Am. Chem. Soc. (1998), pp. 603-604.

Yu, et al., "Tensile Loading of Ropes and Single Wall Carbon Nanotubes . . . ", 84 Phys. Rev. Letters (2000), pp. 5552-5555.

Baughman, et al., "Carbon Nanotubes—The Route Toward Applications", 297 Science (2002), pp. 787-792.

Odom, et al., "Structure and Electronic Properties of Carbon Nanotubes", 104 J. Phys. Chem. B (2000), pp. 2794-2809.

Kong, et al., "Nanotube Molecular Wires as Chemical Sensors", 287 Science (1998), pp. 622-625.

Rao, et al., "Nanotubes", 2 Chem. Phys. Chem. (2001), pp. 78-105.

Gao, et al., "Fabrication and Electron Field Emission Properties of Carbon Nanotube Films . . . ", 13 Adv. Mater. (2001), pp. 1770-1773.

Calvert, "A Recipe for Strength", 399 Nature (1999), pp. 210-211.

Gong, et al., "Surfactant-Assisted Processing of Carbon Nanotube/Polymer Composites", 12 Chem. Mater. (2000), pp. 1049-1052.

Yudasaka, et al., "Effect of an organic polymer in purification and cutting of single-wall carbon nanotubes", 71 Appl. Phys. A (2000), pp. 449-451.

Vigolo, et al., "Macroscopic Fibers and Ribbons of oriented Carbon Nanotubes", 290 Science (2000), pp. 1331-1334.

Coleman, et al., "Phase Seaparation of Carbon nanotubes and Turbostratic Graphite . . . ", 12 Adv. Mater. (2000), pp. 213-216.

Kumar, et al., "Synthesis, Structure, and properties of PBO/SWNT Composites", 35 Macromolecules (2002), pp. 9039-9043.

Kirkwood, et al., "The Visco-elastic Properties of Solutions of Rod-Like Macromolecules," 19 Journal of Chemical Physics (1951), pp. 281-283.

Batchelor, "The Stress System in a suspension of force-free particles", 41 Journal of Fluid Mechanics (1970), pp. 545-547.

O'Connell, et al., "Reversible water-solubilization of single-walled carbon nanotubes by polymer wrapping", 342 Chem. Phys. Letters (2001), pp. 265-271.

Davis, et al., "Phase Behavior and Rheology of SWNTs in Superacids", 37 Macromolecules (2004), pp. 154-160.

Ying, et al., "Functionalization of Carbon nanotubes by Free Radicals", 5 Organic Letters (2003), pp. 1471-1473.

O'Connell, et al., "Band Gap Fluorescence from Individual Single-Walled Carbon Nanotubes," 297 Science (2002), pp. 593-596.

Bachilo, et al., "Structure-Assigned Optical Spectra of Single-Walled Carbon Nanotubes" 298 Science (2002), pp. 2361-2366.

Rols, et al., "Diameter Distribution of Single Wall Carbon Nanotubes in Nanobundles," 18 Eur. Phys. J. B (2000), pp. 201-205.

Bronikowski, et al., "Gas-Phase Production of Carbon . . . ," 19 J. Vac. Sci. & Tech. A-Vacuum Surfaces & Films (2001), pp. 1800-1805.

Kirkwood, et al., "Non-Newtonian Viscoelastic Properties of Rod-Like Macromolecules in Solution", J. Chem. Phys. 24 (1956) pp. 665-669.

Chiang, et al., "Purification and Characterization of Single-Wall Carbon nanotubes . . . ", 105 J. Phys. Chem. B (2001), pp. 8937-8301.

Larson, "The Structure and Rheology of Complex Fluids," Oxford University Press: New York, 1999.

Flory, "Principles of Polymer Chemistry," Cornell University Press: Ithaca, 1953.

* cited by examiner

METHOD AND APPARATUS FOR DETERMINING THE LENGTH OF SINGLE-WALLED CARBON NANOTUBES

CROSS REFERENCE TO RELATED APPLICATIONS

This Application claims priority to U.S. Provisional Patent Application Ser. No. 60/467,642, filed May 2, 2003.

This invention was made with support from the National Science Foundation, Grant Numbers 0134389 and 0073046; and the Office of Naval Research, Grant Number N00014-01-1-0789.

FIELD OF THE INVENTION

The present invention relates generally to carbon nanotubes, and specifically to methods of determining the length of single-wall carbon nanotubes.

BACKGROUND

Single-wall carbon nanotubes (SWNTs) were discovered in 1993 in soot produced in an arc discharge in the presence of transition metal catalysts. See Iijima et al., "Single-Shell Carbon Nanotubes of 1 nm Diameter," *Nature*, 363, pp. 603–605 (1993); Bethune et al., "Cobalt Catalyzed Growth of Carbon Nanotubes with Single Atomic Layer Walls," *Nature*, 363, 605 (1993). Such SWNTs, comprised of a single tube of carbon atoms, are the smallest of the carbon nanotubes. SWNTs can have lengths of up to several micrometers and diameters of approximately 0.5 nm–10.0 nm [Saito et al., *Physical Properties of Carbon Nanotubes*, London: Imperial College Press, 1998; Sun et al., *Nature*, 403: 384 (2000)], although most have diameters of less than 2 nm (Saito et al.). Diameters as small as 0.4 nm have been reported, but these were formed inside either multi-wall carbon nanotubes (MWNTs) [Qin et al., *Chem. Phys. Lett.*, 349: 389–393 (2001)] or zeolites [Wang et al., *Nature*, 408: 50–51 (2000)]. SWNTs, and carbon nanotubes of all types have since been produced by other techniques which include gas-phase reaction methods [Hafner et al., *Chem. Phys. Lett.*, 296: 195–202 (1998); Cheng et al., *Chem. Phys. Lett.*, 289: 602–610 (1998); Nikolaev et al., *Chem. Phys. Lett.*, 313: 91–97 (1999)], laser ablation techniques [Thess et al., *Science*, 273: 483–487 (1996)], and flame synthesis [Vander Wal et al., *J. Phys. Chem. B*, 105(42): 10249–10256 (2001)].

Single-wall carbon nanotubes (SWNTs) have unique structural, electronic and mechanical properties that make them appealing for a variety of applications [Ijima et al., *Nature*, 363, pp. 603–605, 1993; Lansbury et al., *J. Am. Chem. Soc.*, 120, pp. 603–604, 1998; Yu et al., *Phys. Rev. Lett.*, 84, pp. 5552–5555, 2000; Baughman et al., *Science*, 297, pp. 787–792, 2002; Odom et al., *J. Phys. Chem. B*, 104, pp. 2794–2809, 2000; Kong et al., *Science*, 287, pp. 622–625, 1998; Rao et al., *Chem. Phys. Chem.*, 2, pp. 78–105, 2001; Gao et al., *Adv. Mater.*, 13, pp. 1770–1773, 2001]. For instance, the remarkable tensile strength of SWNTs has led to the fabrication of a variety of nanotube-reinforced fibers and composite materials [Calvert, *Nature*, 399, pp. 210–211, 1999; Gong et al., *Chem. Mater.*, 12, pp. 1049–1052, 2000; Yudasaka et al., *Appl. Phys. A*, 71, pp. 449–451, 2000; Vigolo et al., *Science*, 290, pp. 1331–1334, 2000; Coleman et al., *Adv. Mater.*, 12, pp. 213–216, 2000; Kumar et al., *Macromolecules*, 35, pp. 9039–9043, 2002].

Determining the average length of a sample of single-walled carbon nanotubes (SWNTs) is becoming particularly important as the various methods for mass-producing SWNTs are being scaled-up and optimized, and as new methods for chemical and physical cutting are being developed for making SWNTs of prescribed length from the samples produced in the reactors.

Currently, length determination relies chiefly on atomic force microscopy (AFM) measurements, which are time-consuming and suffer the drawbacks of small sample sizes (typically only hundreds of SWNTs) and of possible errors induced by the sample preparation technique (aggregation, preferential adsorption of long or short SWNTs, etc.). Consequently, questions often arise as to how representative the imaged tubes are of a bulk sample. Light scattering has been recently proposed as an alternative method for measuring SWNT length, but this has not yet been proven. Thus, a convenient method for easily and accurately making average length determinations on macroscopic (i.e., bulk) samples of SWNTs would be of great benefit.

SUMMARY

The present invention is directed to a method and apparatus for determining the length of single-wall carbon nanotubes (SWNTs). Such methods and apparatuses generally rely on viscosity measurements in dilute solutions that can then be used to yield the average length of a macroscopic sample of SWNTs. Herein, "average" denotes the square root of the ratio of the third moment and the first moment of the length distribution.

In some embodiments, the present invention is directed to a method generally comprising the steps of: dispersing a sample of SWNTs into a suitable dispersing medium to form a solvent-suspension of solvent-suspended SWNTs; determining the mean SWNT diameter of the solvent-suspended SWNTs; introducing the solvent-suspended SWNTs into a viscosity-measuring device; obtaining a specific viscosity for the SWNT solvent-suspension; and determining the length of the SWNTs based upon the specific viscosity by solving, for example, the Kirkwood-Auer equation corrected by Batchelor's formula for the drag on a slender cylinder for "L," to determine the length of the SWNTs.

In the same or other embodiments, the present invention is directed toward an apparatus for determining the length of SWNTs, wherein the apparatus operates in accordance with the above-described method and generally comprises: a SWNT sample introduction mechanism; a dispersal chamber; a SWNT radius-determination chamber; and a viscosity determining chamber, wherein the SWNT sample introduction mechanism, the dispersal chamber, the SWNT radius-determination chamber, and the viscosity determination chamber are each operatively connected to at least one of the others.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
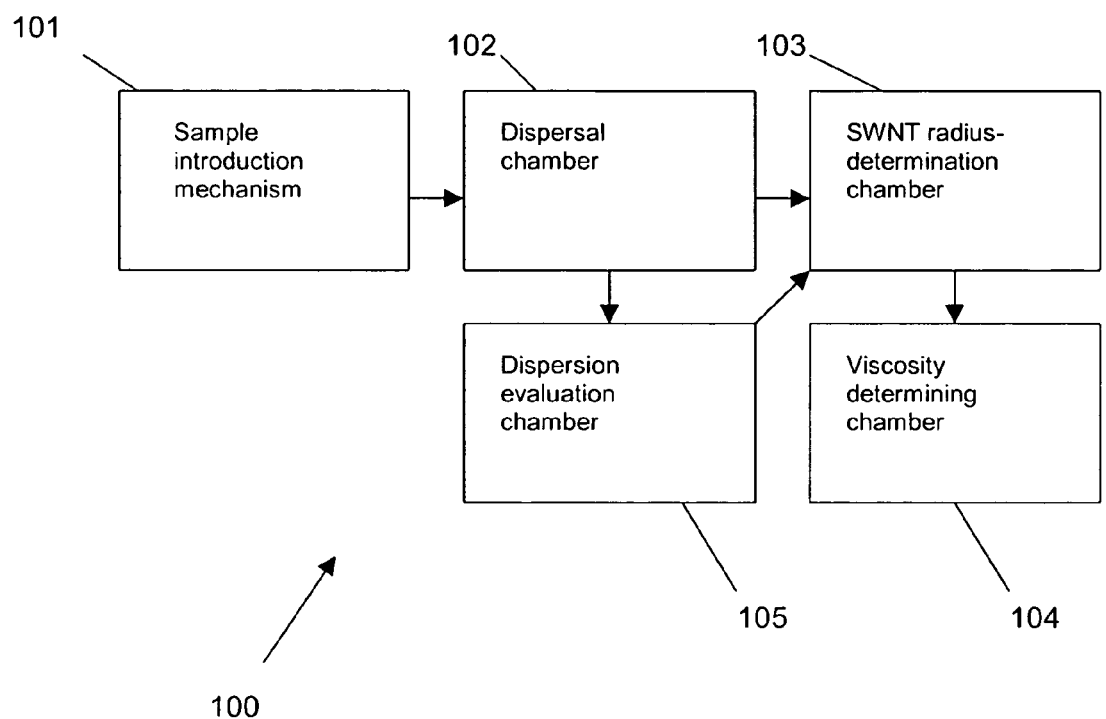
FIG. 1 illustrates in block diagram form an embodiment of an apparatus capable of determining the length of SWNTs in accordance with the principles of the present invention.

While the making and/or using of various embodiments of the present invention are discussed below, it should be appreciated that the present invention provides many applicable inventive concepts that may be embodied in a variety of specific contexts. The specific embodiments discussed herein are merely illustrative of specific ways to make and/or use the invention and are not intended to delimit the scope of the invention.

The present invention is directed toward a method of determining the average length of a macroscopic sample of SWNTs by making viscosity measurements on dilute SWNT solutions/suspensions of that particular sample. Typically, the method (or process) involves the following steps: (1) dispersing a sample of SWNTs into a suitable dispersing medium (referred to herein as a "solvent") to form a solvent-suspension of SWNTs, (2) determining the mean SWNT diameter of the solvent-suspended SWNTs, (3) introducing the solvent-suspended SWNTs into a viscosity-measuring device, (4) obtaining a specific viscosity for the SWNT solvent-suspension, and (5) utilizing the obtained specific viscosity, such as by solving the Kirkwood-Auer equation corrected by Batchelor's formula for the drag on a slender cylinder for "L," to determine the length of the SWNTs. The Kirkwood-Auer equation with the Batchelor correction is hereafter referred to as KAB [Kirkwood and Auer, "The Visco-elastic Properties of Solutions of Rod-Like Macromolecules," *Journal of Chemical Physics*, 19, pp. 281–283 (1951); and Batchelor, *Journal of Fluid Mechanics*, 41, pp. 545–547 (1970)].

Dispersing the SWNTs to form solvent-suspended SWNTs can be done by any known technique. Such techniques include, but are not limited to, surfactant-assisted dispersions (O'Connell et al., *Chem. Phys. Lett.*, 342, 265 (2001)), acid dispersions (Davis et al., "Phase Behavior and Rheology of SWNTs in Superacids," *Macromolecules*, 37, pp. 154–160 (2004)), derivatization-assisted dispersions (Ying et al., *Organic Letters*, 5, pp. 1471–1473 (2003)), and combinations thereof. Dispersal of the SWNTs in a particular solvent medium may require ultrasonic assistance or heating.

In some embodiments of the present invention, the dispersing step may further comprise a step of evaluating whether or not the solvent suspended SWNTs are dispersed individually (i.e., they no longer exist as aggregates or bundles). This can be done by any known technique; fluorescence measurements have been shown to provide excellent verification of SWNT dispersion as individual SWNTs [O'Connell et al., "Band Gap Fluorescence from Individual Single-Walled Carbon Nanotubes," *Science*, 297, pp. 593–596 (2002); Bachilo et al., "Structure-Assigned Optical Spectra of Single-Walled Carbon Nanotubes," *Science*, 298, pp. 2361–2366 (2002)].

Determining the mean SWNT diameter and radius "R" of the solvent-suspended SWNTs can be done by any known technique, including, but not limited to, scanning probe microscopy, electron microscopy, electron diffraction, X-ray diffraction, luminescence spectroscopy, Raman spectroscopy, and combinations thereof. The SWNT "breathing mode" in Raman spectra is commonly used to determine the average diameter of SWNTs in bulk samples [Rols et al., "Diameter distribution of single wall carbon nanotubes in nanobundles," *Eur. Phys. J. B*, 18, pp. 201–205 (2000)].

It will be apparent to those of skill in the art that the introduction of the solvent-suspended SWNTs into a viscosity-measuring device is dependent upon the type and model of device used. The viscosity-measuring device can be any device capable of determining the viscosity of the solvent-suspended SWNTs. Such devices include, but are not limited to, rheometers and capillary viscometers. In some embodiments, a rotational rheometer is used. In some embodiments, a capillary viscometer, such as but not limited to a cross-arm viscometer, is used. If a capillary viscometer is used, the size is chosen so as to be appropriate for the solvent viscosity and the length of the SWNTs being evaluated. ASTM standard sizes exist, see American Society for Testing and Materials.

In obtaining a specific viscosity for the SWNT solvent-suspension, devices such as rotational rheometers (both stress- and strain-controlled types) provide absolute measurements, as they measure zero-shear viscosity. Capillary viscometers, on the other hand, measure shear-thinning viscosity or absolute viscosity depending on their size; the shear-thinning viscosity is only a relative measurement. Consequently, the latter technique would require standardization. By measuring the viscosity of both the solvent ($\eta_{solvent}$) and the solvent+SWNTs ($\eta$), the specific viscosity ($\eta_{sp}$) can be determined by:

$$\eta_{sp} = (\eta - \eta_{solvent})/(\eta_{solvent})$$

With the specific viscosity in hand, KAB can be solved for "L" to determine the length of the SWNTs:

$$\eta_{sp} = \frac{\eta - \eta_{solvent}}{\eta_{solvent}} = \frac{(L/R)^2}{22.5[\ln(L/R_H)]}\left[\left(\frac{1 + \frac{0.64}{\ln(L/R_H)}}{1 - \frac{1.5}{\ln(L/R_H)}}\right) + \frac{1.659}{(\ln(L/R_H))^2}\right]\phi$$

Where R=SWNT average radius, $R_H$=SWNT hydrodynamic radius, and $\phi$=SWNT volume fraction. Note that R is obtained as described above, $R_H$ is dependent upon the dispersion technique, and $\phi$, the volume fraction, is a function of the mass concentration "c" that can be calculated by $\phi=c/\rho$, where $\rho$ is the mass density of SWNTs. This is a non-linear equation that can be solved using any technique or procedure capable of solving non-linear equations. Such techniques include, but are not limited to, programs like MATLAB and MATHEMATICA. Because of the large aspect ratios SWNTs possess, these measurements are only marginally sensitive to the estimated value of $R_H$. Consequently, even if the estimate for $R_H$ is off by 1 nanometer (nm) or so (this is a large error since the SWNTs typically are 0.7–2.0 nm in diameter), the length measurement is only off by a few percent.

The present invention is also directed to an apparatus for implementing the processes described above. Referring to FIG. 1, apparatus 100, for determining the length of SWNTs, comprises: a SWNT sample introduction mechanism 101 (such as a mechanism operable to perform one or more of essentially any method of physically introducing said sample into the apparatus, and may include weight and volume determinations); a dispersal chamber 102 for generating a solvent-suspension of SWNTs; a SWNT radius-determination chamber 103 (such as a chamber operable to perform one or more of any technique or procedure previously mentioned that is capable of making such determinations); and a viscosity-determining chamber 104 (such as a chamber that may include a viscometer, rheometer, or other such device capable of measuring the viscosity of the solvent-suspended SWNTs. Apparatus 100 can optionally include a dispersion evaluation chamber 105, such as a chamber that may include a fluorescence measuring device. Included in apparatus 100 is a transport mechanism for transferring the SWNT sample into and out of the various chambers. Such transport mechanisms may comprise pumps and valves to accomplish the transport of material from one chamber to the next.

The following examples are provided to more fully illustrate some of the embodiments of the present invention. The examples illustrate methods by which SWNT lengths can be measured. It should be appreciated by those of skill in the art that the techniques disclosed in the examples which follow represent techniques discovered by the inventors to function well in the practice of the invention, and thus can be considered to constitute exemplary modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

SWNTs produced by the HiPco method [Bronikowski et al., "Gas-Phase Production of Carbon Single-Walled Nanotubes from Carbon Monoxide via the HiPco Process: A Parametric Study," *J. Vac. Sci.& Tech. A-Vacuum Surfaces& Films*, 19, pp. 1800–1805 (2001)] were suspended as individuals by sonication in a solution of 2% PLURONICS (PEO-PPO-PEO) surfactants, followed by decanting (PLURONICS is a Registered Trademark of BASF Corporation). Fluorescence measurements established that over 90% of the SWNTs were dispersed as individuals, with a mean diameter of 0.93 nm. The dispersion of SWNTs was diluted progressively from 130 to 25 ppm wt. The zero-shear viscosity of each dispersion was measured with a strain-controlled rheometer. The difference between the viscosity of the dispersion and that of the solvent (water plus 2% PLURONICS) was found to be a linear function of concentration (determined by evaluating the viscosity as a function of concentration), as predicted by KAB for Brownian rod-like particles. See Kirkwood et al., *J. Chem. Phys.*, 19, pp. 281–283 (1951); Kirkwood et al., *J. Chem. Phys.*, 24, pp. 665–669 (1956); Batchelor, *Journal of Fluid Mechanics*, 41, pp. 545–547 (1970). By using KAB the length of the SWNTs was determined to be 570±30 nm.

EXAMPLE 2

The results obtained in the aqueous dispersion stabilized by the PLURONICS surfactant were compared with the viscosity measurements of purified SWNTs (Chiang et al.,*J. Phys. Chem. B*, 105, pp. 8397–8301, 2001) dispersed in 102% $H_2SO_4$ (2 wt. % excess $SO_3$) at concentrations below 90 ppm wt. Like the PLURONICS/aqueous dispersion, measurements on the acid-dispersed SWNTs also show a linear relationship between viscosity and concentration, and KAB yields an average length of approximately 570 nm. Although no fluorescence measurements are available in acids to determine whether the SWNTs are truly dispersed as individuals, the viscosity measurements suggest that most SWNTs are indeed individually dispersed in sulfuric acid at these low concentrations.

EXAMPLE 3

This example shows how, in the case of SWNTs stabilized by a surfactant, $R_H$ can be estimated for use in KAB, and how the determined length is only marginally sensitive to the estimated value of $R_H$. See FIG. 2, where SWNT 200 is stabilized by PEO 201 and PPO 202 of a PLURONIC surfactant.

Figure 2:
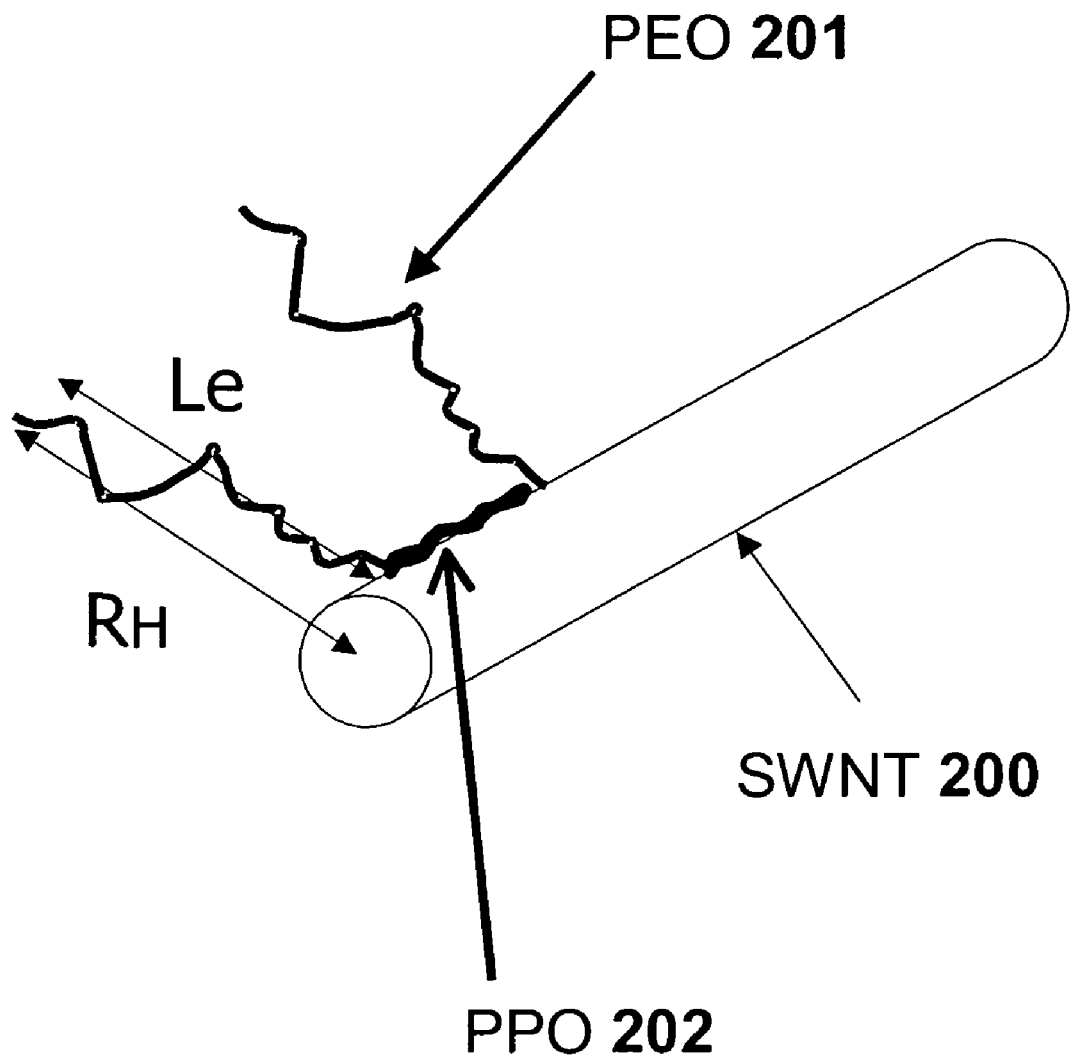
FIG. 2 schematically illustrates the hydrodynamic radius $R_H$ of SWNTs when they are dispersed with the help of surfactants.

Referring to FIG. 2, for a PEO-PPO-PEO F68 PLURONIC surfactant, if:

Mw=8400

Length of PEO unit L=0.24 nm (reference data available in polymer handbooks)

N PEO units=76 (This is the number of PEO units, specified by the manufacturer of the PLURONICS; the PLURONICS have a formula $(PEO)_N-(PPO)_M-(PEO)_N$; the numbers N and M identify the type of PLURONIC and are available from the manufacturer (BASF))

$Le=(N)^{3/5}L=3.2$ nm (This formula is a standard way of estimating the size of a polymer molecule once the length of the unit L and the number of units N are known. See Larson, R. G., *The Structure and Rheology of Complex Fluids*, Oxford University Press: New York, 1999; Flory, P. J., *Principles of Polymer Chemistry*, Cornell University Press: Ithaca, 1953.)

R (SWNT)=0.5 nm (from fluorescence)

$R_H$=R+Le=3.7 nm

Figure 3:
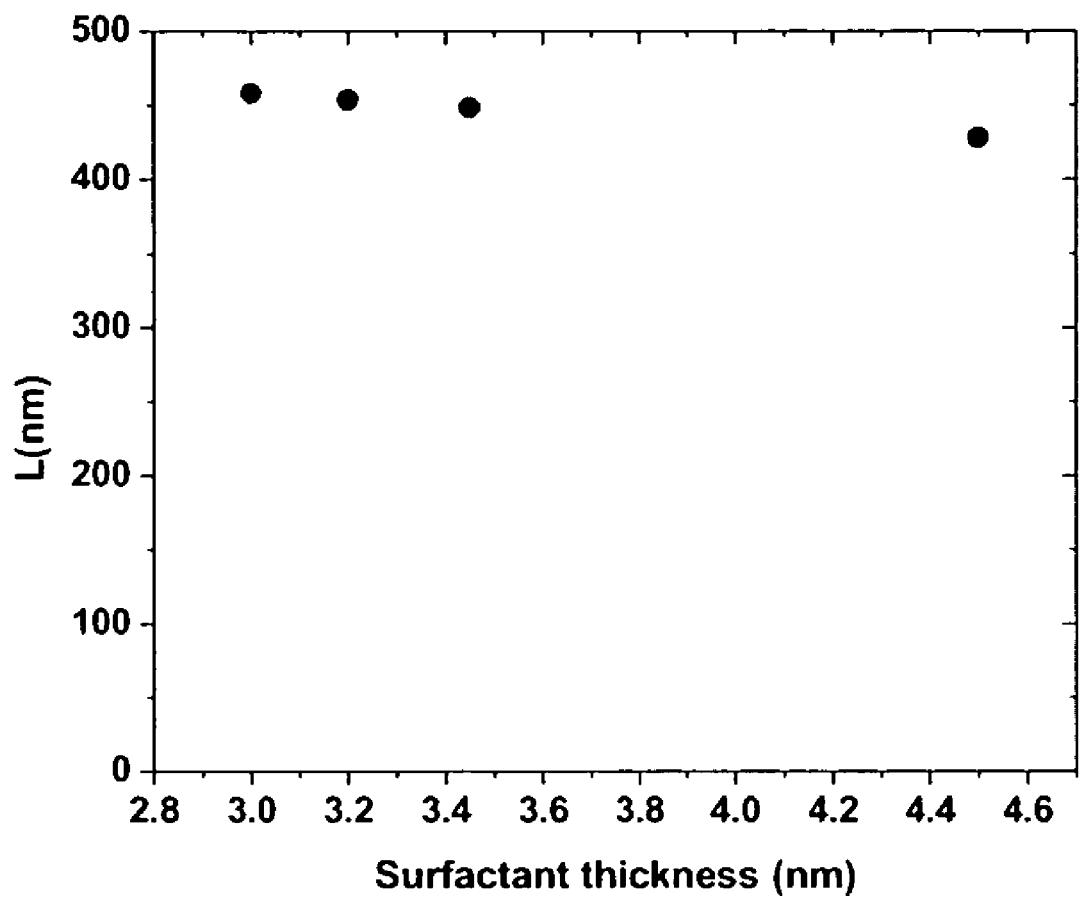
FIG. 3 illustrates in graphical form the length determination of SWNTs versus the surfactant thickness.

Referring to FIG. 3, it can be seen that the length determined for SWNTs ("L") is only marginally sensitive to the value used for the surfactant thickness.

EXAMPLE 4

This example compares the data obtained using a capillary viscometer with that obtained using a rotational rheometer.

Figure 4:
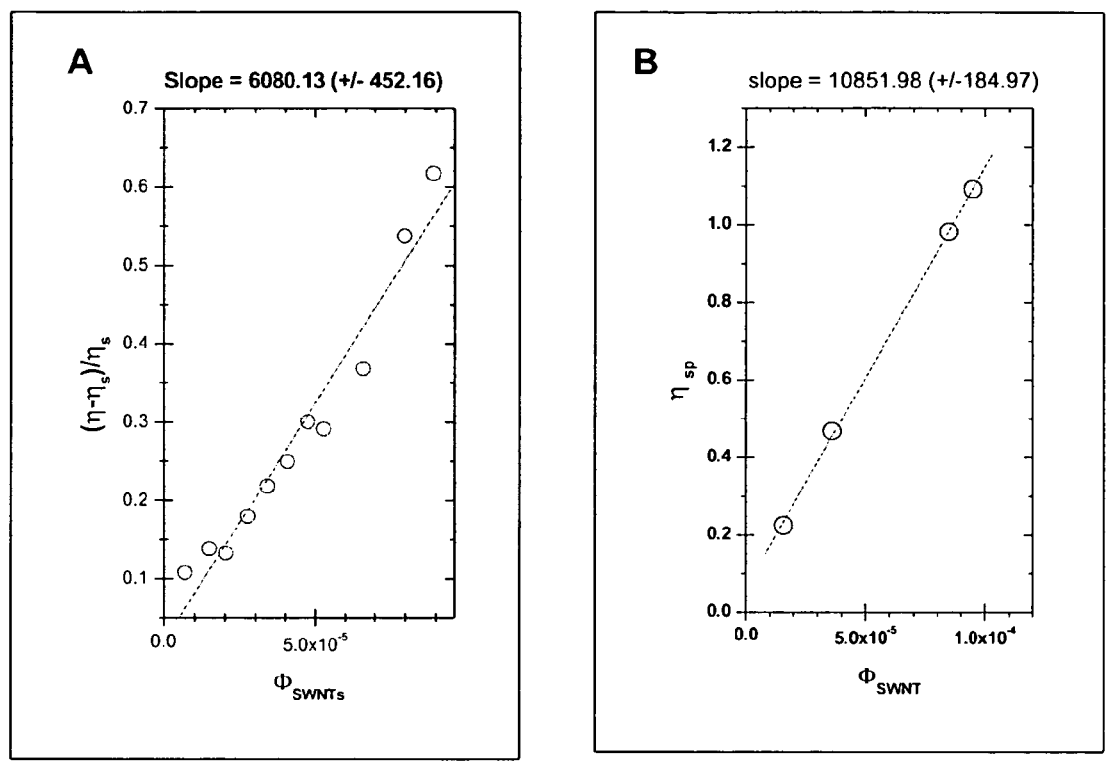
FIG. 4 illustrates in graphical form the specific viscosity of the SWNTs versus the SWNT concentration obtained with a capillary viscometer (A), and a rotational rheometer (B)

Referring to FIG. 4, plot "A" represents data obtained with a capillary viscometer, whereas plot "B" represents data obtained with a rotational rheometer. While the data obtained with the rheometer seems somewhat better, in both cases the specific viscosity ($\eta_{sp}$) can be said to vary linearly with SWNT concentration ($\phi$).

Table 1 shows the length determination from two different measurements and explains why an absolute measurement is obtained with the rotational rheometer (zero-shear viscosity is measured), and why a relative measurement is obtained with the capillary viscometer (shear-thinning viscosity is measured). The shear rate in the capillary was found to be approximately 70 to 100 $s^{-1}$; the measurements obtained with the rotational rheometer indicated that shear thinning was occurring at shear rates above 20 s$^{-1}$.

TABLE 1

| Rotational Rheometer (zero-shear viscosity) | Capillary Viscometer (viscosity in shear-thinning region) |
|---|---|
| R = 0.635 nm | R = 0.635 nm |
| $R_H$ = 3.7 nm | $R_H$ = 3.7 nm |
| L = 570 nm | L = 404 nm |
| L/R = 900 | L/R = 636 |

EXAMPLE 5

This Example serves to illustrate the good agreement the present methods have when different surfactants are used, and the good agreement the present methods have with the much more time consuming AFM method.

Figure 5:
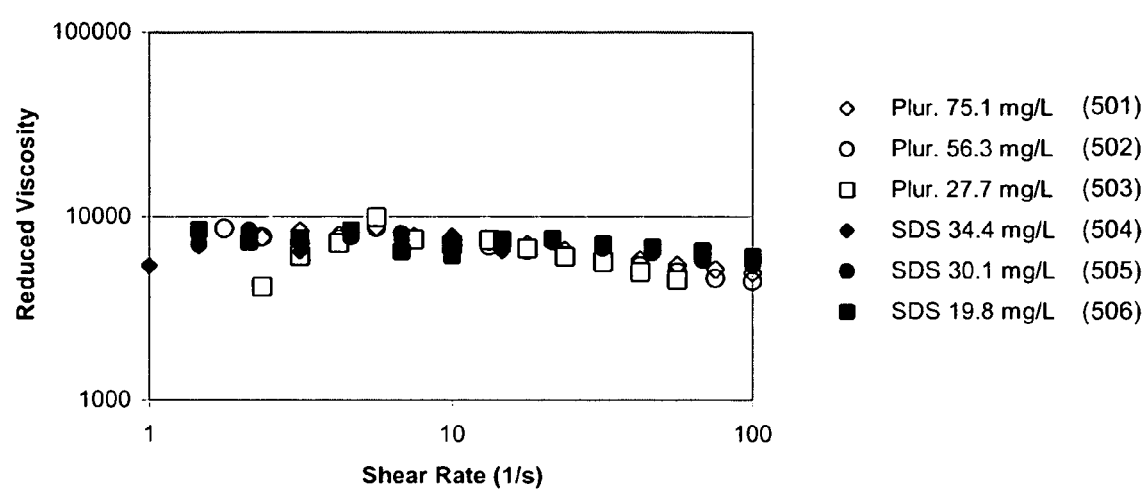
FIG. 5 illustrates how the reduced viscosities for both the PLURONICS system and the SDS system are in excellent agreement.

SWNTs from HiPco batch HPR 120.3 were dispersed in both 2 wt. % PLURONICS (F68) and 0.5 wt. % sodium dodecylsulfate (SDS), each concentration above the critical micell concentration (CMC, the smallest concentration at which the surfactant forms micelles) for the respective surfactant. The samples were sonicated and decanted to produce individual SWNTs, by the method previously discussed [O'Connell et al., Chem. Phys. Lett., 342, 265 (2001)]. As in Example 1, the two solutions were diluted progressively at concentrations from 75 to 19 ppm wt. As shown in FIG. 5 (for concentrations 501–506), the reduced viscosities for both systems overlay with excellent agreement. Using the KAB equation, the aspect ratio is found by evaluating the zero-shear reduced viscosity, by the plateau at low shear rates. The average lengths were 570±30 for PLURONICS and 565±30 for SDS.

Figure 6:
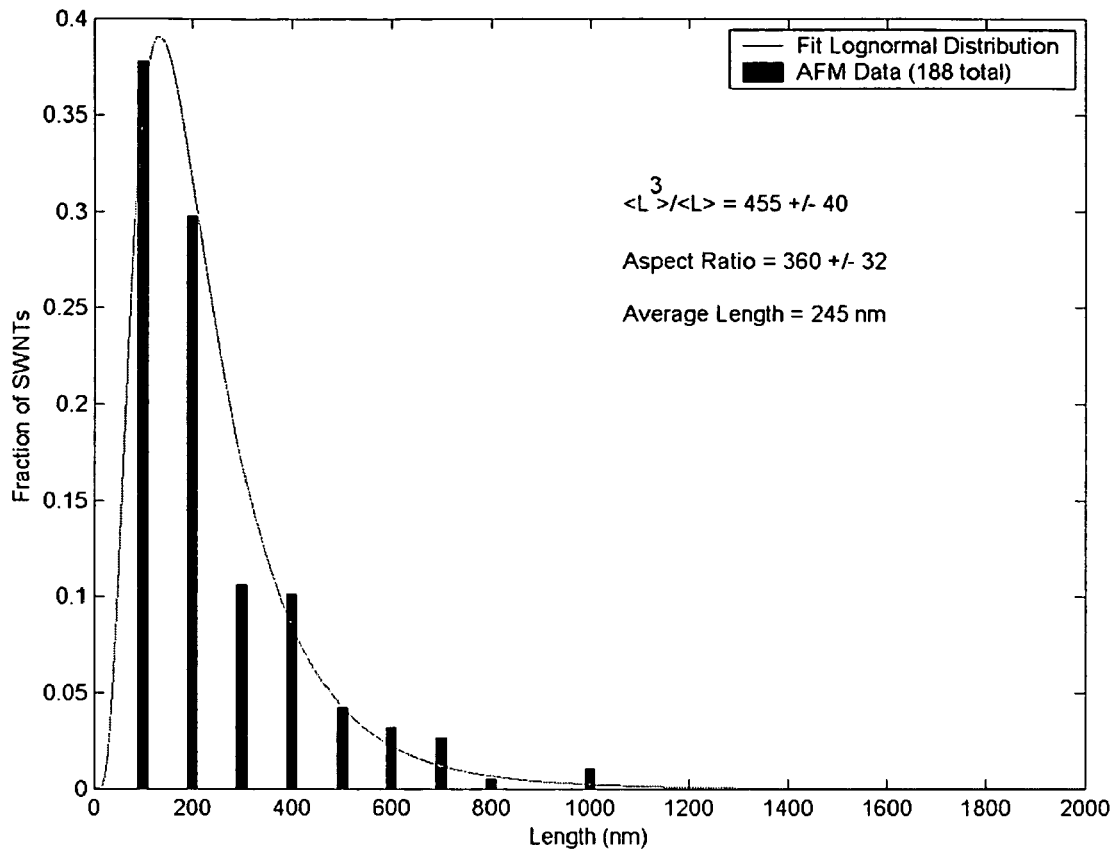
FIG. 6 depicts a histogram of 188 AFM-determined individual SWNT lengths fit to a lognormal distribution curve.

The dispersions in PLURONICS were deposited on aminated silicon wafers by dipping the wafer into the dispersion and rinsing with isopropanol and nanopure water. The wafers were then imaged by an Atomic Force Microscope (AFM) in tapping mode. Sufficient images were taken to produce a histogram of 188 individual SWNTs. A lognormal distribution was then fit to the distribution with good agreement (within 15%), as shown in FIG. 6. The third moment, first moment and the average length were determined from the lognormal length distribution. From the fit distribution the zero-shear viscosity can be evaluated to determine the aspect ratio by the method discussed previously. The average length from the AFM data was found to be 457±40, which is within 20% of that found by using KAB above. Considering that AFM measurements suffer from errors due to sample preparation and small sample size (hundreds of SWNTs), the agreement of the viscosity and AFM techniques is good.

EXAMPLE 6

This Example serves to illustrate the consistency of the present method in analyzing production runs that have been designed to yield SWNTs of substantially different average length.

SWNTs produced by the HiPco method at two different reactor conditions designated by batch numbers HPR 120.5 and HPR 126.2 were dispersed in fuming $H_2SO_4$ without any prior purification. The reactor conditions used to produce HPR 126.2 were expected to result in shorter tubes. Each dispersion was diluted progressively from 300 to 40 ppm wt and the viscosity measured in a strain controlled rotational rheometer. The dilute regime where KAB applies is characterized by overlap of the reduced viscosity data and constant rotational relaxation time. The average lengths were determined to be 1765±254 for HPR 120.5 and 790±230 for HPR 126.2. The lower average length for HPR 126.2 is in accordance with expectations based on HiPco reaction theory and AFM measurements. This data shows that while the presence of impurities (~30% by wt. SWNT) increases measurement error, the method can be used to deduce changes in aspect ratio.

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A method for determining the length of single-wall carbon nanotubes comprising the steps of:
   (a) dispersing a sample of SWNTs into a suitable dispersing medium to form a solvent-suspension of solvent-suspended SWNTs;
   (b) obtaining the mean SWNT diameter of the solvent-suspended SWNTs;
   (c) introducing the solvent-suspended SWNTs into a viscosity-measuring device;
   (d) obtaining a specific viscosity for the SWNT solvent-suspension; and
   (e) determining the length of the SWNTs based upon the specific viscosity.

2. The method of claim 1, further comprising a step of evaluating whether the solvent-suspended SWNTs are dispersed individually.

3. The method of claim 2, wherein the step of evaluating is done using fluorescence measurements.

4. The method of claim 1, wherein the step of dispersing comprises the use of a surfactant.

5. The method of claim 1, wherein the step of dispersing comprises a dispersing technique selected from the group consisting of polymer wrapping, chemical derivatization, acid protonation, and combinations thereof.

6. The method of claim 1, wherein the step of dispersing comprises chemical derivatization selected from the group consisting of sidewall functionalization, end functionalization, and combinations thereof.

7. The method of claim 1, wherein the step of dispersing involves ultrasonication.

8. The method of claim 1, wherein the step of obtaining the mean SWNT diameter involves a technique selected from the group consisting of Raman spectroscopy, scanning probe microscopy, electron microscopy, electron diffraction, X-ray diffraction, luminescence spectroscopy, and combinations thereof.

9. The method of claim 1, wherein the viscosity-measuring device is a capillary viscometer.

10. The method of claim 9 further comprising a step of standardizing the capillary viscometer.

11. The method of claim 1, wherein the viscosity-measuring device is a rheometer.

12. The method of claim 1, wherein the step of determining the length of the SWNTs comprises solving KAB for rods for "L."

13. An apparatus for determining the length of SWNTs comprising:
(a) a SWNT sample introduction mechanism;
(b) a dispersal chamber;
(c) a SWNT radius-determination chamber; and
(d) a viscosity determining chamber, wherein the SWNT sample introduction mechanism, the dispersal chamber, the SWNT radius-determination chamber, and the viscosity determination chamber are each operatively connected to at least one of the others.

14. The apparatus of claim 13, wherein the dispersal chamber provides solvent-suspended SWNTs.

15. The apparatus of claim 13, wherein the dispersal chamber utilizes ultrasonication to disperse SWNTs.

16. The apparatus of claim 13, further comprising a dispersion evaluation chamber operatively connected to at least one of the SWNT sample introduction mechanism, the dispersal chamber, the SWNT radius-determination chamber, and the viscosity determination chamber.

17. The apparatus of claim 16, wherein the dispersion evaluation chamber utilizes luminescence spectrosopy to provide verification of SWNT dispersion as individual SWNTs.

18. The apparatus of claim 13, wherein the radius-determination chamber utilizes a technique selected from the group consisting of Raman spectroscopy, scanning probe microscopy, electron microscopy, electron diffraction, X-ray diffraction, luminescence spectroscopy, and combinations thereof, to determine the mean radius of the SWNTs in the sample.

19. The apparatus of claim 13, wherein the viscosity determining chamber comprises a viscosity measuring device selected from the group consisting of a capillary viscometer, a rheometer, and combinations thereof.

20. The apparatus of claim 13, further comprising a computer operatively connected to at least one of the SWNT sample introduction mechanism, the dispersal chamber, the SWNT radius-determination chamber, the viscosity determination chamber, and the dispersion evaluation chamber such that it can receive a viscosity measurement, wherein the computer is operable to determine the length of the SWNTs based upon the viscosity measurement.

21. A method for determining the relative length of single-wall carbon nanotubes comprising the steps of:
(a) dispersing a sample of SWNTs into a suitable dispersing medium to form a solvent-suspension of solvent-suspended SWNTs;
(b) introducing the solvent-suspended SWNTs into a viscosity-measuring device;
(c) obtaining a viscosity for the SWNT solvent-suspension; and
(d) comparing the viscosity to viscosities obtained for other SWNT solvent-suspensions.

* * * * *